United States Patent
Wang et al.

(10) Patent No.: US 7,289,883 B2
(45) Date of Patent: *Oct. 30, 2007

(54) APPARATUS AND METHOD FOR PATIENT ROUNDING WITH A REMOTE CONTROLLED ROBOT

(75) Inventors: Yulun Wang, Goleta, CA (US); Louis Kavoussi, Lutherville, MD (US)

(73) Assignee: InTouch Technologies, Inc., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/650,149

(22) Filed: Jan. 5, 2007

(65) Prior Publication Data

US 2007/0112464 A1    May 17, 2007

Related U.S. Application Data

(63) Continuation of application No. 10/751,032, filed on Jan. 2, 2004, now Pat. No. 7,164,969, which is a continuation-in-part of application No. 10/206,457, filed on Jul. 25, 2002, now Pat. No. 6,925,357.

(51) Int. Cl.
*G06F 19/00* (2006.01)

(52) U.S. Cl. ............ 700/245; 700/246; 700/250; 700/254; 700/260; 700/261; 700/262; 318/568.12; 901/1; 901/2; 702/188

(58) Field of Classification Search ............ 700/245, 700/246, 254, 260, 261, 262, 250; 318/568.12; 901/1, 2; 702/188
See application file for complete search history.

(56) References Cited

U.S. PATENT DOCUMENTS 3,821,995 A    7/1974    Aghnides (Continued)

FOREIGN PATENT DOCUMENTS

CA    2289697 A1    11/1998

(Continued)

OTHER PUBLICATIONS

Bauer et al., Remote telesurgical mentoring: feasibility and efficacy, 2000, IEEE, p. 1-9.*

(Continued)

*Primary Examiner*—Thomas Black
*Assistant Examiner*—McDieunel Marc
(74) *Attorney, Agent, or Firm*—Ben J. Yorks; Irell & Manella LLP

(57) ABSTRACT

A method for remotely monitoring a patient. The method includes generating and transmitting input commands to the robot from a remote station. The remote station may include a personal computer that is operated by a doctor. The input commands can move the robot so that a video image and sounds of the patient can be captured by a robot camera and microphone, respectively, and transmitted back to the remote station. The robot may also have a monitor and a speaker to allow for two-way videoconferencing between the patient and a doctor at the remote station. The robot can move from room to room so that a doctor can make "patient rounds" within a medical facility. The system thus allows a doctor visit patients from a remote location, thereby improving the frequency of visits and the quality of medical care.

10 Claims, 10 Drawing Sheets

U.S. PATENT DOCUMENTS

| | | |
|---|---|---|
| 4,413,693 A | 11/1983 | Derby |
| 4,471,354 A | 9/1984 | Smith |
| 4,519,466 A | 5/1985 | Shiraishi |
| 4,638,445 A | 1/1987 | Mattaboni |
| 4,709,265 A | 11/1987 | Silverman et al. |
| 4,733,737 A | 3/1988 | Falamak |
| 4,803,625 A | 2/1989 | Fu et al. |
| 4,875,172 A | 10/1989 | Kanayama |
| 4,977,971 A | 12/1990 | Crane, III et al. |
| 5,073,749 A | 12/1991 | Kanayama |
| 5,084,828 A | 1/1992 | Kaufman et al. |
| 5,130,794 A | 7/1992 | Ritchey |
| 5,186,270 A | 2/1993 | West |
| 5,305,427 A | 4/1994 | Nagata |
| 5,341,242 A | 8/1994 | Gilboa et al. |
| 5,341,457 A | 8/1994 | Hall, II et al. |
| 5,341,854 A | 8/1994 | Zezulka et al. |
| 5,374,879 A | 12/1994 | Pin et al. |
| 5,419,008 A | 5/1995 | West |
| 5,441,047 A | 8/1995 | David et al. |
| 5,462,051 A | 10/1995 | Oka et al. |
| 5,486,853 A | 1/1996 | Baxter et al. |
| 5,510,832 A | 4/1996 | Garcia |
| 5,544,649 A | 8/1996 | David et al. |
| 5,553,609 A | 9/1996 | Chen et al. |
| 5,572,229 A | 11/1996 | Fisher |
| 5,630,566 A | 5/1997 | Case |
| 5,636,218 A | 6/1997 | Ishikawa et al. |
| 5,701,904 A | 12/1997 | Simmons et al. |
| 5,762,458 A | 6/1998 | Wang et al. |
| 5,786,846 A | 7/1998 | Hiroaki |
| 5,802,494 A | 9/1998 | Kuno |
| 5,836,872 A | 11/1998 | Kenet et al. |
| 5,838,575 A | 11/1998 | Lion |
| 5,857,534 A | 1/1999 | DeValult et al. |
| 5,871,451 A | 2/1999 | Unger et al. |
| 5,917,958 A | 6/1999 | Nunally et al. |
| 5,959,423 A | 9/1999 | Nakanishi et al. |
| 5,966,130 A | 10/1999 | Benman, Jr. |
| 6,006,946 A | 12/1999 | Williams et al. |
| 6,036,812 A | 3/2000 | Williams et al. |
| 6,133,944 A | 10/2000 | Braun et al. |
| 6,135,228 A | 10/2000 | Asada et al. |
| 6,170,929 B1 | 1/2001 | Wilson et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,233,735 B1 | 5/2001 | Ebihara |
| 6,259,806 B1 | 7/2001 | Green |
| 6,292,713 B1 | 9/2001 | Jouppi et al. |
| 6,304,050 B1 | 10/2001 | Skaar et al. |
| 6,325,756 B1 | 12/2001 | Webb et al. |
| 6,346,950 B1 | 2/2002 | Jouppi |
| 6,369,847 B1 | 4/2002 | James et al. |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,463,361 B1 | 10/2002 | Wang et al. |
| 6,474,434 B1 | 11/2002 | Bech |
| 6,491,701 B2 | 12/2002 | Tierney et al. |
| 6,496,099 B2 | 12/2002 | Wang et al. |
| 6,507,773 B2 | 1/2003 | Parker et al. |
| 6,522,906 B1 | 2/2003 | Salisbury et al. |
| 6,532,404 B2 | 3/2003 | Colens |
| 6,535,182 B2 | 3/2003 | Stanton |
| 6,535,793 B2 | 3/2003 | Allard |
| 6,543,899 B2 | 4/2003 | Covannon et al. |
| 6,549,215 B2 | 4/2003 | Jouppi |
| 6,581,798 B2 | 6/2003 | Liff et al. |
| 6,587,750 B2 | 7/2003 | Gerbi et al. |
| 6,594,552 B1 | 7/2003 | Nowlin et al. |
| 6,646,677 B2 | 11/2003 | Noro et al. |
| 6,684,129 B2 | 1/2004 | Salisbury et al. |
| 6,799,065 B1 | 9/2004 | Niemeyer |
| 6,804,656 B1 | 10/2004 | Rosenfeld et al. |
| 6,839,612 B2 | 1/2005 | Sanchez et al. |
| 6,840,904 B2 | 1/2005 | Goldberg |
| 6,914,622 B1 | 7/2005 | Smith et al. |
| 6,995,664 B1 | 2/2006 | Darling |
| 2001/0037163 A1 | 11/2001 | Allard |
| 2001/0054071 A1 | 12/2001 | Loeb |
| 2002/0027597 A1 | 3/2002 | Sachau |
| 2002/0057279 A1 | 5/2002 | Jouppi |
| 2002/0058929 A1 | 5/2002 | Green |
| 2002/0063726 A1 | 5/2002 | Jouppi |
| 2002/0120362 A1 | 8/2002 | Lathan et al. |
| 2002/0130950 A1 | 9/2002 | James et al. |
| 2002/0141595 A1 | 10/2002 | Jouppi |
| 2002/0183894 A1 | 12/2002 | Wang et al. |
| 2003/0050733 A1 | 3/2003 | Wang et al. |
| 2003/0060808 A1 | 3/2003 | Wilk |
| 2003/0135203 A1 | 7/2003 | Wang et al. |
| 2003/0151658 A1 | 8/2003 | Smith |
| 2004/0143421 A1* | 7/2004 | Wang et al. ............ 702/188 |
| 2004/0162637 A1* | 8/2004 | Wang et al. ............ 700/245 |
| 2006/0047365 A1* | 3/2006 | Ghodoussi et al. ...... 700/251 |

FOREIGN PATENT DOCUMENTS

| | | |
|---|---|---|
| EP | 0981905 B1 | 1/2002 |
| JP | 07-257422 A | 10/1995 |
| JP | 08-084328 A | 3/1996 |
| JP | 2000-032319 A | 1/2000 |
| JP | 2002-046088 | 2/2002 |
| JP | 2002-305743 A | 10/2002 |

OTHER PUBLICATIONS

Salemi et al., MILO: personal robot platform, 2005, IEEE, p. 4089-4094.*

Johns Hopkins Medical Institutions| Stephenson, Dr. Robot Tested at Hopkins, 2003, Internet, p. 1-2.*

F. Ando et al., "A Multimedia Self-service Terminal with Conferencing Functions", 1995, IEEE, pp. 357-362.

Bar-Cohen et al., Virtual reality robotic telesurgery simulations using MEMICA haptic system, Mar. 5, 2001, Internet, pp. 1-7.

Bauer, John et al., "Remote telesurgical mentoring: feasibility and efficicacy", 2000, IEEE, pp. 1-9.

Brooks, Rodney, Abstracts from Flesh & Machines, How Robots Will Change Us, "Remote Presence", p. 131-147, Feb. 2002.

Celi et al., "The eICU: It's not just telemedicine", Critical Care Medicine, vol. 29, No. 8 (Supplement), Aug. 2001.

Cleary et al., "State of the art in surgical robotics: Clinical applications and technology challenges", Feb. 24, 2002 Internet, pp. 1-26.

CNN, Floating 'droids' to roam space corridors of the future, Jan. 12, 2000, Internet, pp. 1-4.

Davies, "Robotics in Minimally Invasive Surgery", 1995, Internet, pp. 5/1-5/2.

Elhajj et al., "Supermedia in Internet-based telerobotic operations", 2001, Internet, pp. 1-14.

Goldberg et al., "Collaborative Teleoperation via the Internet", IEEE International Conference on Robotics and Automation, Apr. 2000, San Francisco, California.

Goldman, Lea, "Machine Dreams", Entrepreneurs, Forbes, May 27, 2002.

Gump, Michael D., "Robot Technology Improves VA Pharmacies", 2001, Internet, pp. 1-3.

Harmo et al., "Moving Eye—Interactive Telepresence Over Internet With a Ball Shaped Mobile Robot", 2000.

Hees, William P., "Communications Design for a Remote Presence Robot", Jan. 14, 2002.

Ishihara, Ken et al., "Intelligent Microrobot DDS (Drug Delivery System) Measured and Controlled by Ultrasonics", Nov. 3-5, 1991, IEEE/RSJ, pp. 1145-1150, vol. 2.

Kanehiro, Fumio et al., Virtual Humanoid Robot Platform to Develop Controllers of Real Humanoid Robots without Porting, 2001,IEEE, pp. 3217-3276.

Lim, Hun-ok et al., Control to Realize Human-like Walking of a Biped Humanoid Robot, IEE 2000, pp. 3271-3276.

Loeb, Gerald, "Virtual Visit: Improving Communication for Those Who Need It Most", 2001.

Mack, "Minimally invasive and robotic surgery", 2001, Internet IEEE, pp. 568-572.

Magne Charge—Smart Power for Electric Vehicles, Internet, Jun. 27, 2002.

McCardle et al., "The challenge of utilizing new technology in design education", 2000 Internet, pp. 122-127.

Nakajima et al., "A Multimedia Teleteaching System sing an Electronic Whiteboard for Two-Way Communication of Motion Videos and Chalkboards",IEEE , pp. 436-441.

Ogata et al., "Development of Emotional Communication Robot: WAMOEBA-2r—Esperimental evaluation . . . ", 2000 IEEE, pp. 175-180.

Ojha, Anad, "An application of Virtual Reality in Rehabilitation", Jan. 1994, IEEE, pp. 4-6.

Paulos et al., "A World Wide Web Telerobotic Remote Environment Browser", http://vive.cs.berkeley.edu/capek, 1995.

Paulos, Eric John, "Personal Tele-Embodiment", Fall 2001.

Paulos, et al. , "Ubiquitous Tele-embodiment: Applications and Implications", International Journal of Human Computer Studies, Jun. 1997, vol. 46, No. 6, pp. 861-877.

Paulos, et al., "Designing Personal Tele-Embodiment", Presented at the IEEE International Conference on Robotics and Animation, Leuven, Belgium, May 20, 1998.

Pin et al., "A New Family of Omnidirectional and Holonomic Wheeled Platforms for Mobile Robots", IEEE, vol. 10, No. 4, Aug. 1994.

Robot Hardware Mobile Robotics Research Group, Edinburgh, "Mobile Robotics Research Group", 2000 Internet, pp. 1-2.

Roy et al., "Towards Personal Service Robots for the Elderly", Internet, Mar. 7, 2002.

Sandt, Frederic et al., "Perceptions for a Transport Robot in Public Environments", 1997, IROS '97.

Shimoga et al., Touch and force reflection for telepresence surgery, 1994, IEEE, pp. 1049-1050.

Tendick et al., "Human-Machine Interfaces for Minimally Invasive Surgery", 1997, IEEE, pp. 2771-2776.

Thrun et al, "Probabilistic Algorithms and the Interactive Museum Tour-Guide Robot Minerva", 2000, Internet pp. 1-35.

Tzafestas, et al., "VR-based Teleoperation of a Mobile Robotic Assistant: Progress Report", 2000, Internet, pp. 1-23.

Weiss et al., Telework and video-mediated communication: Importance of real-time, interactive communication for workers with disabilities, 1999, Internet, pp. 1-4.

Yamasaki et al., Applying Personal Robots and Active Interface to Video Conference Systems, 1995, Internet, pp. 243-248.

Yong et al., "Robot task execution with telepresence using virtual reality technology", 1998, Internet, pp. 1-9.

Zipperer, Lorri, "Robotic dispensing system", 1999, Internet, pp. 1-2.

Zorn, Benjamin G., "Ubiquitous Telepresence", http://www.cs.colorado.edu/~zorn/ut/vision.html, Mar. 5, 1996.

* cited by examiner

APPARATUS AND METHOD FOR PATIENT ROUNDING WITH A REMOTE CONTROLLED ROBOT

CROSS REFERENCE TO RELATED APPLICATIONS

This application is a continuation of application Ser. No. 10/751,032, filed on Jan. 2, 2004, now U.S. Pat. No. 7,164,969 which is a continuation-in-part of application Ser. No. 10/206,457, filed on Jul. 25, 2002, now U.S. Pat. No. 6,925,357:

BACKGROUND OF THE INVENTION

1. Field of the Invention

The subject matter disclosed generally relates to the field of robotics.

2. Background Information

Patient consultation is a critical component of medical care. For example, it is typically imperative that a physician visit a patient after a surgical procedure. Such visits not only allow the physician to observe the patient for follow-up care, but aids in establishing the all important personal relationship between doctor and patient. Because of various economic and regulatory issues it has become increasing difficult for physicians to develop strong relationships with patients through interactive visits.

John Hopkins Medical Institution has tested a program where tele-conferencing equipment is placed in a patient's room. The doctor can then remotely "visit" the patient through the tele-conferencing system. Such an approach would require tele-conferencing equipment in each patient room, thereby increasing the cost of equipping and maintaining the medical facility. Additionally, the tele-conferencing equipment must be placed in a position to allow the doctor to view the patient. This may be in a location adjacent to the patient's bed. Such a location may not allow the doctor to view an ambulatory patient.

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope which has a camera that allows a surgeon to view a surgical area of a patient.

Tele-robots such as hazardous waste handlers and bomb detectors may contain a camera that allows the operator to view the remote site. Canadian Pat. No. 2289697 issued to Treviranus, et al. discloses a videoconferencing platform that has both a camera and a monitor. The Treviranus patent also discloses embodiments with a mobile platform, and mechanisms for moving the camera and the monitor.

Publication Application No. US-2003-0050233-A1 discloses a remote robotic system wherein a plurality of remote stations can control a plurality of robotic arms used to perform a minimally invasive medical procedure. Each remote station can receive a video image provided by the endoscope inserted into the patient. The remote stations are linked to the robotic system by a dedicated communication link.

To date there has not been a utilization of mobile robots to allow a doctor to remotely visit a patient. Such a technique would allow more frequent doctor/patient visits and improve the quality of medical care.

BRIEF SUMMARY OF THE INVENTION

A method for remotely monitoring a patient with a robot that has a camera and a microphone. A robot input command is generated and transmitted from a remote station. The robot input command is received by the robot. The robot moves in response to the robot input command. A video image and sound of the patient is transmitted to the remote station from the robot.

DETAILED DESCRIPTION

Disclosed is a method for remotely monitoring a patient. The method includes generating and transmitting input commands to the robot from a remote station. The remote station may include a personal computer that is operated by a doctor. The input commands can move the robot so that a video image and sounds of the patient can be captured by a robot camera and microphone, respectively, and transmitted back to the remote station. The robot may also have a monitor and a speaker to allow for two-way videoconferencing between the patient and a doctor at the remote station. The robot can move from room to room so that a doctor can make "patient rounds" within a medical facility. The system thus allows a doctor to visit patients from a remote location, thereby improving the frequency of visits and the quality of medical care.

Figure 1:
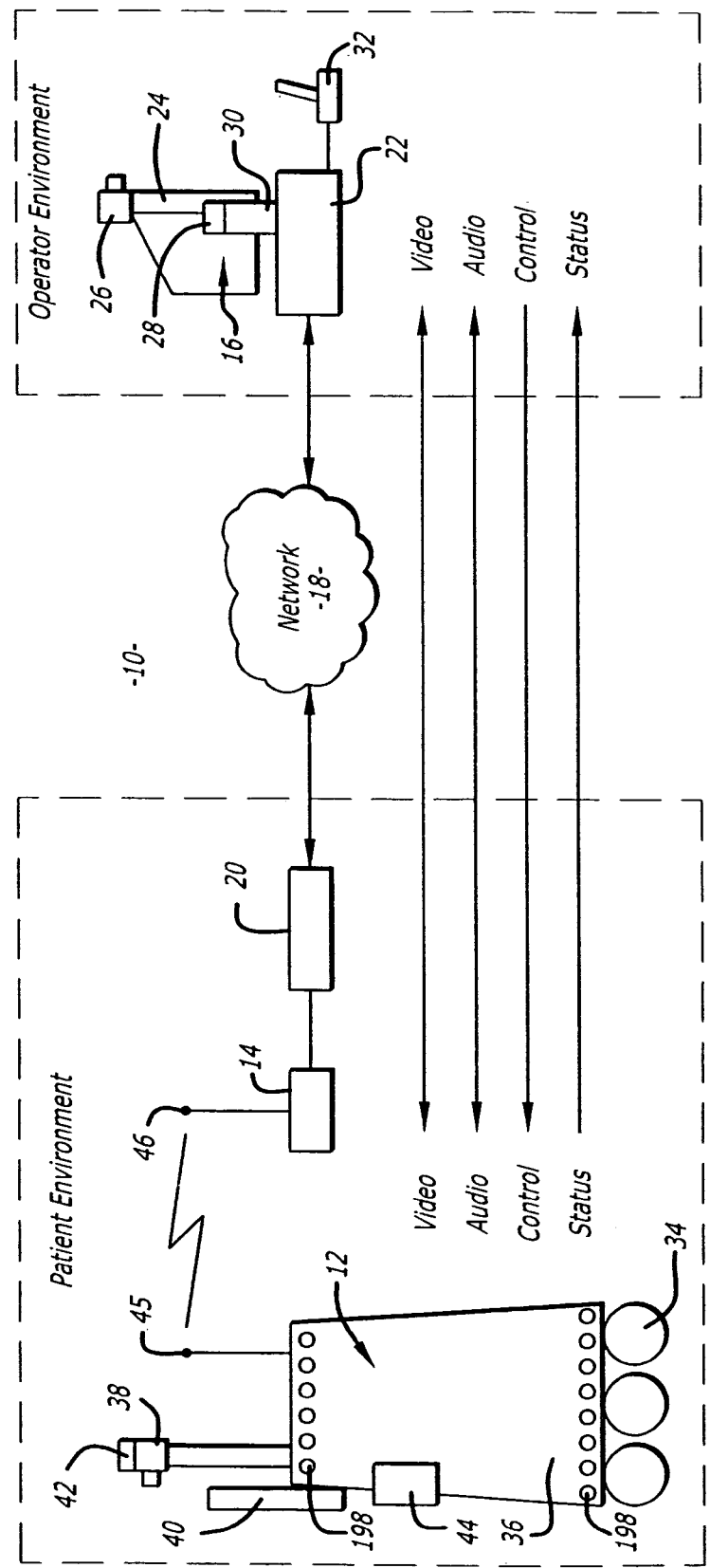
FIG. 1 is an illustration of a robotic system.

Referring to the drawings more particularly by reference numbers, FIG. 1 shows a robotic system 10. The robotic system 10 includes a robot 12, a base station 14 and a remote control station 16. The control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device.

The remote control station 16 may include a computer 22 that has a monitor 24, a camera 26, a microphone 28 and a speaker 30. The computer 22 may also contain an input device 32 such as a joystick or a mouse. The station 16 is typically located in a place that is remote from the robot 12. Although only one robot 12 is shown, it is to be understood that the system 10 may have a plurality of robots 12. In general any number of robots 12 may be controlled by any number of remote stations. For example, one remote station 16 may be coupled to a plurality of robots 12, or one robot 12 may be coupled to a plurality of remote stations 16.

The robot 12 includes a movement platform 34 that is attached to a robot housing 36. Also attached to the robot housing 36 are a camera 38, a monitor 40, a microphone(s) 42 and a speaker 44. The microphone 42 and speaker 30 may create a stereophonic sound. The robot 12 may also have an antenna 45 that is wirelessly coupled to an antenna 46 of the base station 14. The system 10 allows a user at the remote control station 16 to move the robot 12 through the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

Each remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

The system 10 may be the same or similar to a robotic system sold by the assignee InTouch-Health, Inc. of Santa Barbara, Calif. under the trademark COMPANION.

Figure 2:
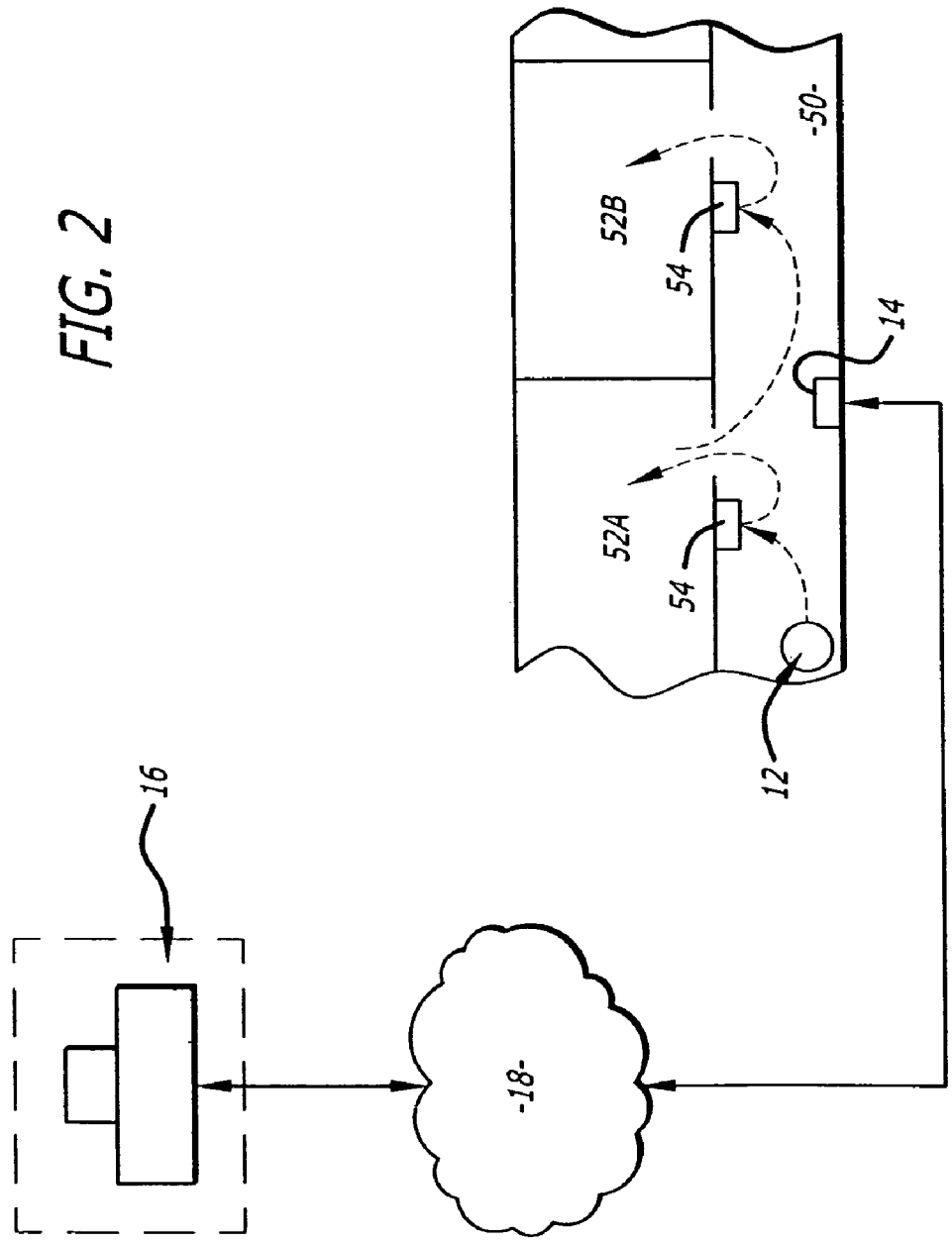
FIG. 2 is a schematic showing movement of a robot in a medical facility.

FIG. 2 shows an implementation of the system in a medical facility 50. The medical facility 50 may be a hospital, assisted living home, etc, that contains a plurality of patient rooms 52, including a first patient room 52A and a second patient room 52B, each containing one or more patients.

A doctor may be located at a remote station 16. The remote station 16 may be on or off the premises of the medical facility 50. The station 16 is linked to the robot 12 by the network 18 and wireless base station 14. The medical facility 50 may have a number of wireless base stations 14 located throughout the facility 50 so that the robot 12 is always linked to a station 14.

The system 10 allows the doctor to make patient rounds in the facility 50. For example, the doctor may generate robot input commands at the remote station 16 that are then transmitted and received by the robot 12. The input commands may cause the robot to move to the door of the first patient room 52A. The doctor can view a chart 54 outside the room through the robot camera. The doctor may utilize a zoom feature of the camera to read the chart.

After reading the chart the doctor may move the robot into the first patient room 52A. The system allows the doctor to conduct a two-way videoconference with the patient. The videoconference may allow the doctor to observe the patient through the robot camera. The doctor can also ask questions that can be generated by the robot speaker and/or displayed by the robot monitor. The robot monitor can display the doctor at the remote station so that the patient feels they are being "visited" by the doctor.

After the visiting the patient in the first patient room 52A the doctor can move the robot 12 to the second patient room 52B where the process is repeated. The system thus allows the doctor to visit multiple patients from a remote location. This increases the frequency of doctor visits, reduces doctor fatigue and improves the overall medical care of the patients.

Figure 3:
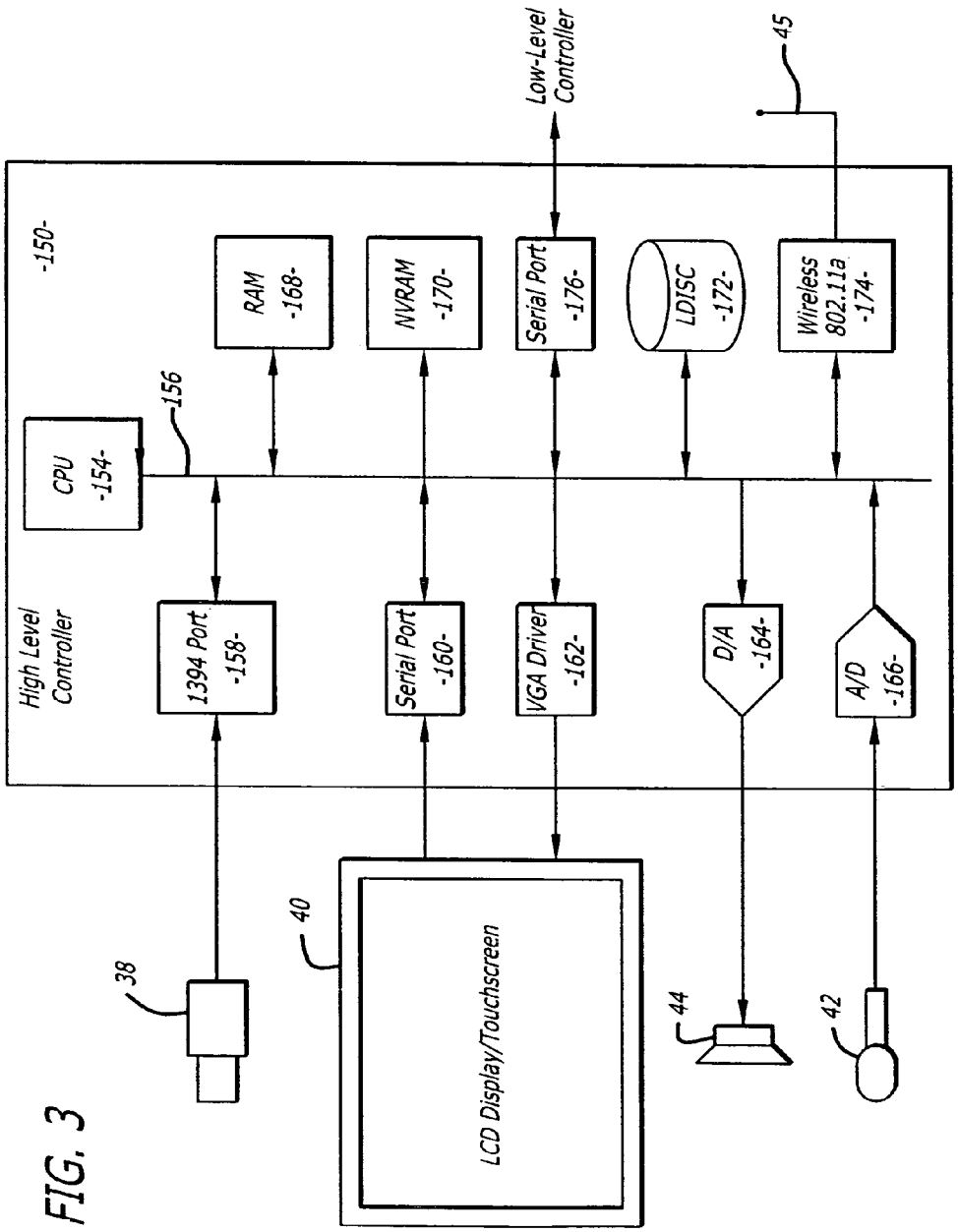
FIG. 3 is a schematic of an electrical system of a robot.
Figure 4:
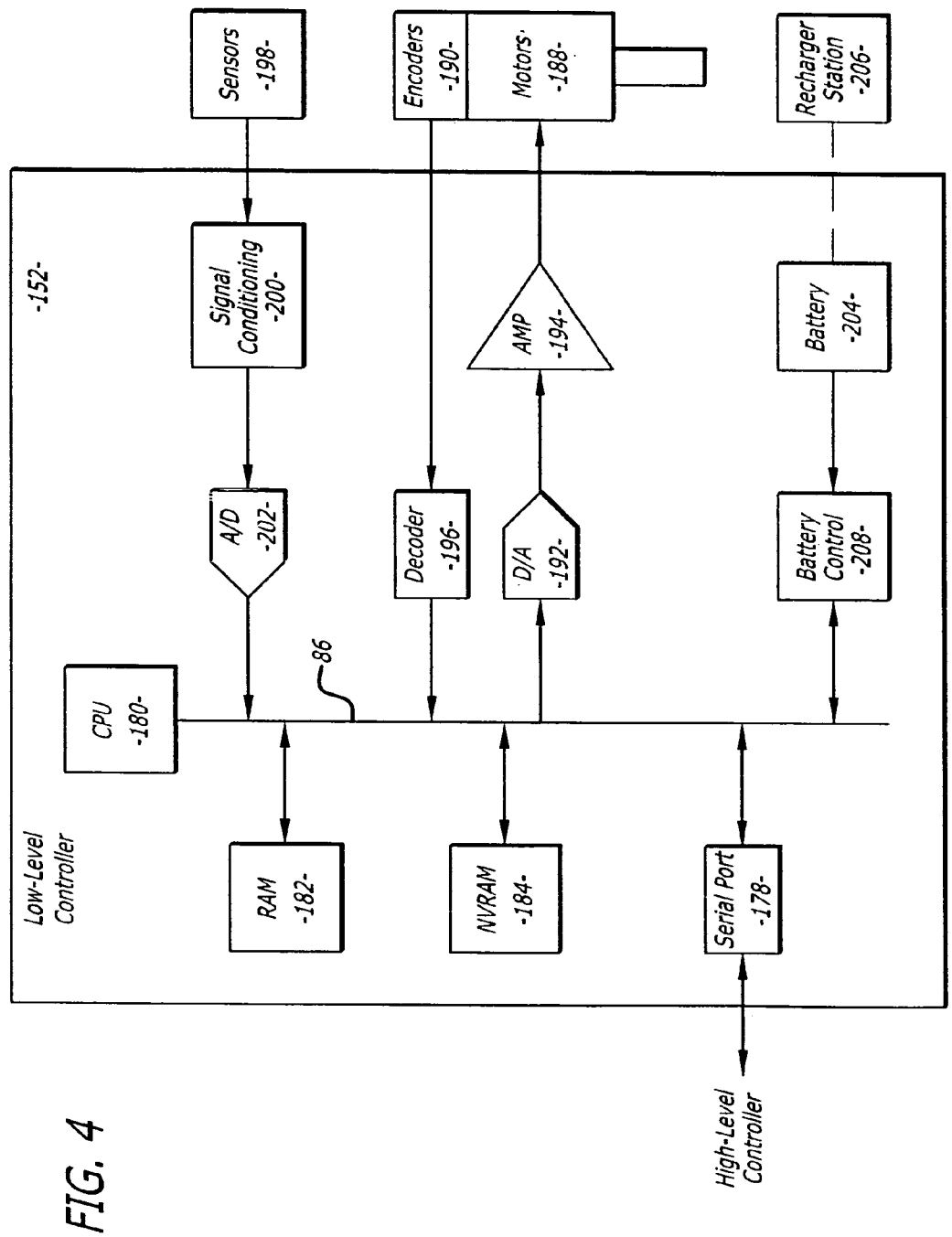
FIG. 4 is a further schematic of the electrical system of the robot.

FIGS. 3 and 4 show an embodiment of the robot 12. The robot 12 may include a high level control system 150 and a low level control system 152. The high level control system 150 may include a processor 154 that is connected to a bus 156. The bus 156 is coupled to the camera 38 by an input/output (I/O) port 158, and to the monitor 40 by a serial output port 160 and a VGA driver 162. The monitor 40 may include a touchscreen function that allows the patient to enter input by touching the monitor screen 40.

The speaker 44 is coupled to the bus 156 by a digital to analog converter 164. The microphone 42 is coupled to the bus 156 by an analog to digital converter 166. The high level controller 150 may also contain random access memory (RAM) device 168, a non-volatile RAM device 170 and a mass storage device 172 that are all coupled to the bus 162. The mass storage device 172 may contain medical files of the patient that can be accessed by the user at the remote control station 16. For example, the mass storage device 172 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 174. By way of example, the transceiver 174 may transmit and receive information in accordance with IEEE 802.11b.

The controller 154 may operate with a LINUX OS operating system. The controller 154 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 150 operates to control the communication between the robot 12 and the remote control station 16.

The high level controller 150 may be linked to the low level controller 152 by serial ports 176 and 178. The low level controller 152 includes a processor 180 that is coupled to a RAM device 182 and non-volatile RAM device 184 by a bus 186. The robot 12 contains a plurality of motors 188 and motor encoders 190. The encoders 190 provide feedback information regarding the output of the motors 188. The motors 188 can be coupled to the bus 186 by a digital to analog converter 192 and a driver amplifier 194. The encoders 190 can be coupled to the bus 186 by a decoder 196. The robot 12 also has a number of proximity sensors 198 (see also FIG. 1). The position sensors 198 can be coupled to the bus 186 by a signal conditioning circuit 200 and an analog to digital converter 202.

The low level controller 152 runs software routines that mechanically actuate the robot 12. For example, the low level controller 152 provides instructions to actuate the movement platform to move the robot 12. The low level controller 152 may receive movement instructions from the high level controller 150. The movement instructions may be received as movement commands from the remote control station. Although two controllers are shown, it is to be understood that the robot 12 may have one controller controlling the high and low level functions.

The various electrical devices of the robot 12 may be powered by a battery(ies) 204. The battery 204 may be recharged by a battery recharger station 206 (see also FIG. 1). The low level controller 152 may include a battery control circuit 208 that senses the power level of the battery 204. The low level controller 152 can sense when the power falls below a threshold and then send a message to the high level controller 150. The high level controller 150 may include a power management software routine that causes the robot 12 to move so that the battery 204 is coupled to the recharger 206 when the battery power falls below a threshold value. Alternatively, the user can direct the robot 12 to the battery recharger 206. Additionally, the battery 204 may be replaced or the robot 12 may be coupled to a wall power outlet by an electrical cord (not shown).

Figure 5:
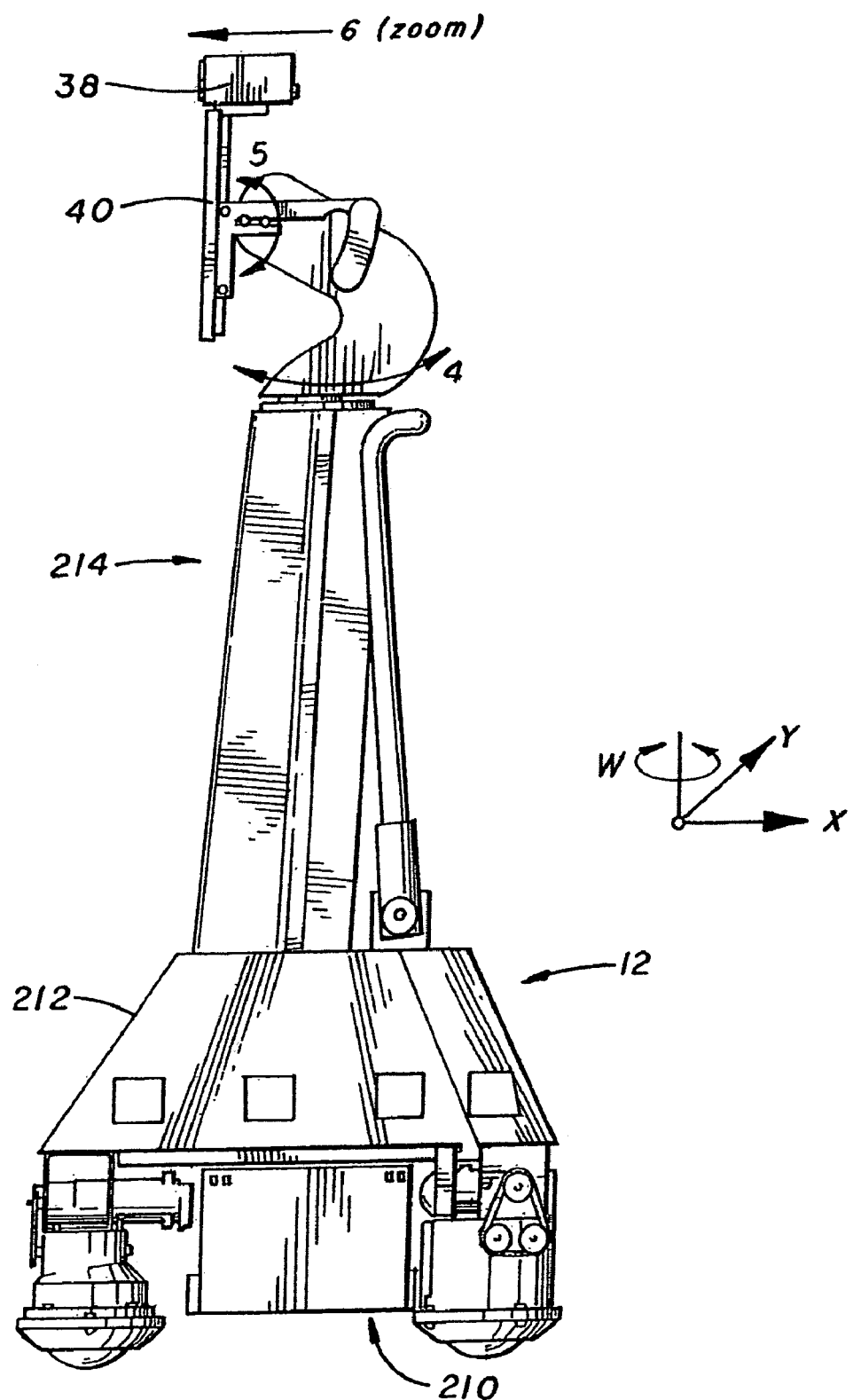
FIG. 5 is side view of the robot.

FIG. 5 shows an embodiment of the robot 12. The robot 12 may include a holonomic platform 210 that is attached to a robot housing 212. The holonomic platform 210 provides three degrees of freedom to allow the robot 12 to move in any direction.

The robot 12 may have a pedestal assembly 214 that supports the camera 38 and the monitor 40. The pedestal assembly 214 may have two degrees of freedom so that the camera 26 and monitor 24 can be swiveled and pivoted as indicated by the arrows.

Figure 6:
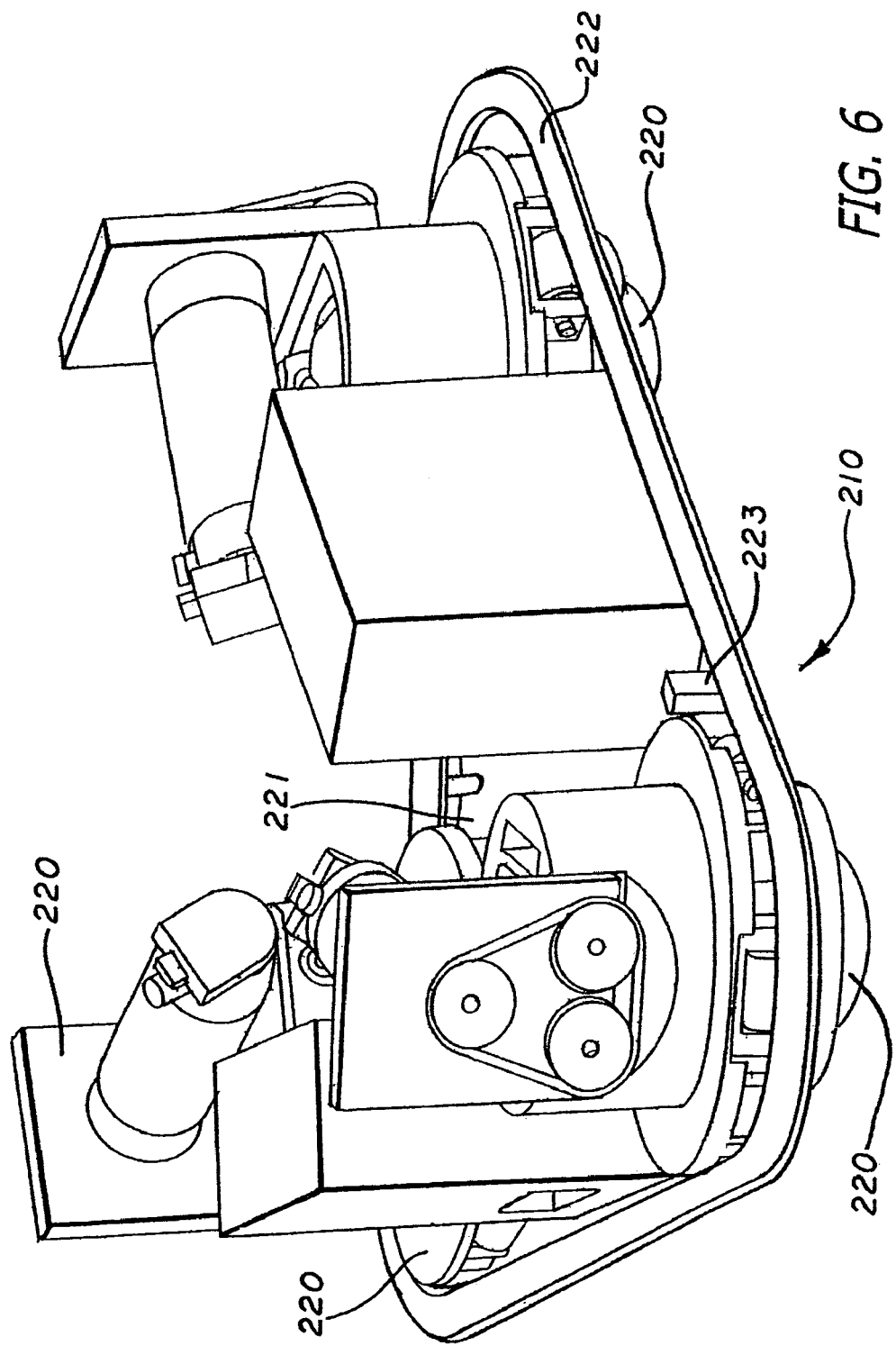
FIG. 6 is a top perspective view of a holonomic platform of the robot.

As shown in FIG. 6 the holonomic platform 210 may include three roller assemblies 220 that are mounted to a base plate 221. The roller assemblies 220 allow for movement in any direction.

The robot housing 212 may include a bumper 222. The bumper 222 may be coupled to optical position sensors 223 that detect when the bumper 222 has engaged an object. After engagement with the object the robot can determine the direction of contact and prevent further movement into the object.

Figure 7:
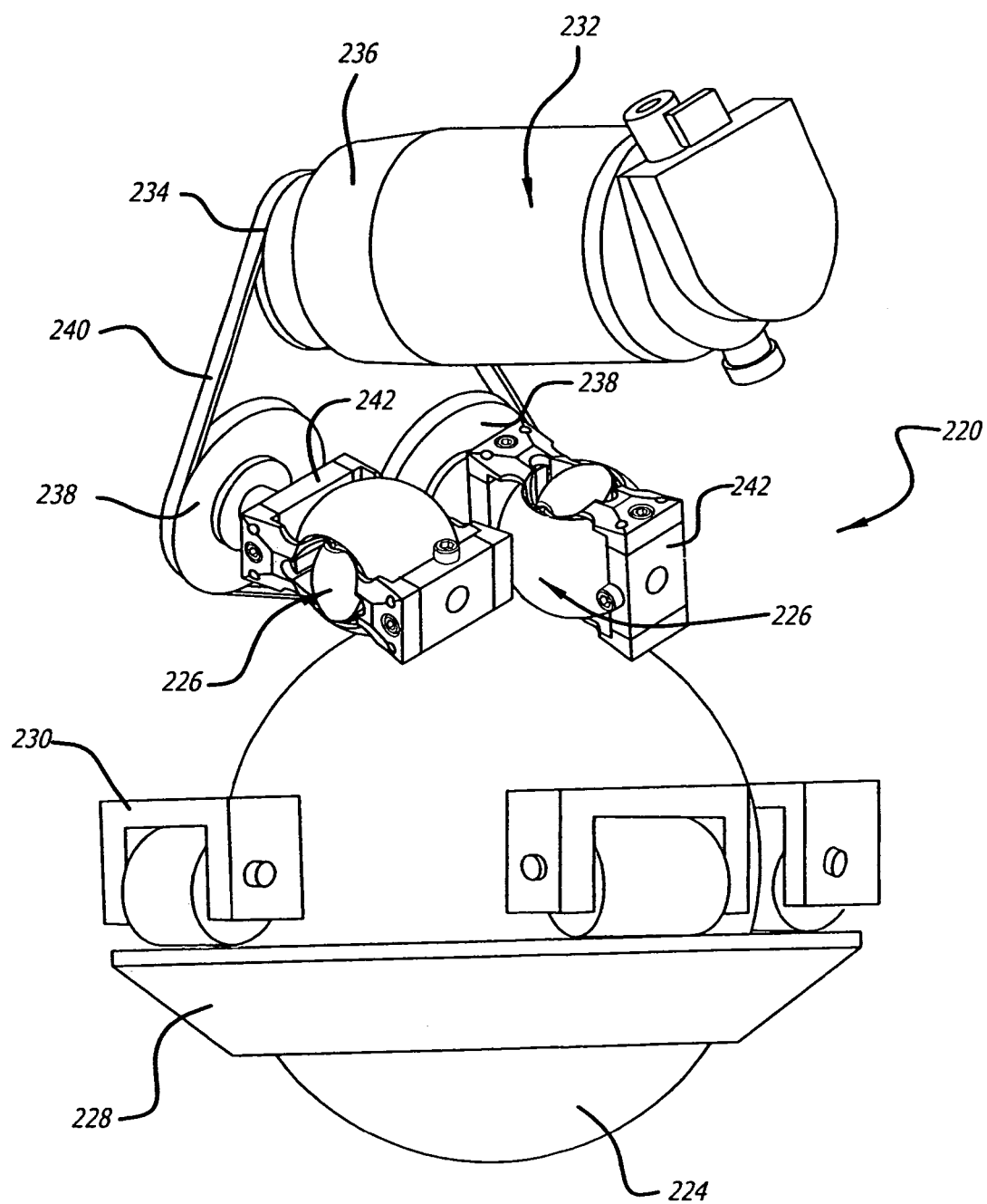
FIG. 7 is aside perspective view of a roller assembly of the holonomic platform.

FIG. 7 shows an embodiment of a roller assembly 220. Each assembly 220 may include a drive ball 224 that is driven by a pair of transmission rollers 226. The assembly 220 may include a retainer ring 228 and a plurality of bushings 230 that capture and allow the ball 224 to rotate in x and y directions but prevent movement in a z direction. The assembly also holds the ball under the transmission rollers 226.

The transmission rollers 226 are coupled to a motor assembly 232. The assembly 232 corresponds to the motor 188 shown in FIG. 4. The motor assembly 232 includes an output pulley 234 attached to a motor 236. The output pulley 234 is coupled to a pair of ball pulleys 238 by a drive belt 240. The ball pulleys 238 are each attached to a transmission bracket 242. The transmission rollers 226 are attached to the transmission brackets 242.

Rotation of the output pulley 234 rotates the ball pulleys 238. Rotation of the ball pulleys 238 causes the transmission rollers 226 to rotate and spin the ball 224 through frictional forces. Spinning the ball 224 will move the robot 12. The transmission rollers 226 are constructed to always be in contact with the drive ball 224. The brackets 242 allow the transmission rollers 226 to freely spin in a direction orthogonal to the driven direction when one of the other roller assemblies 220 is driving and moving the robot 12.

Figure 8:
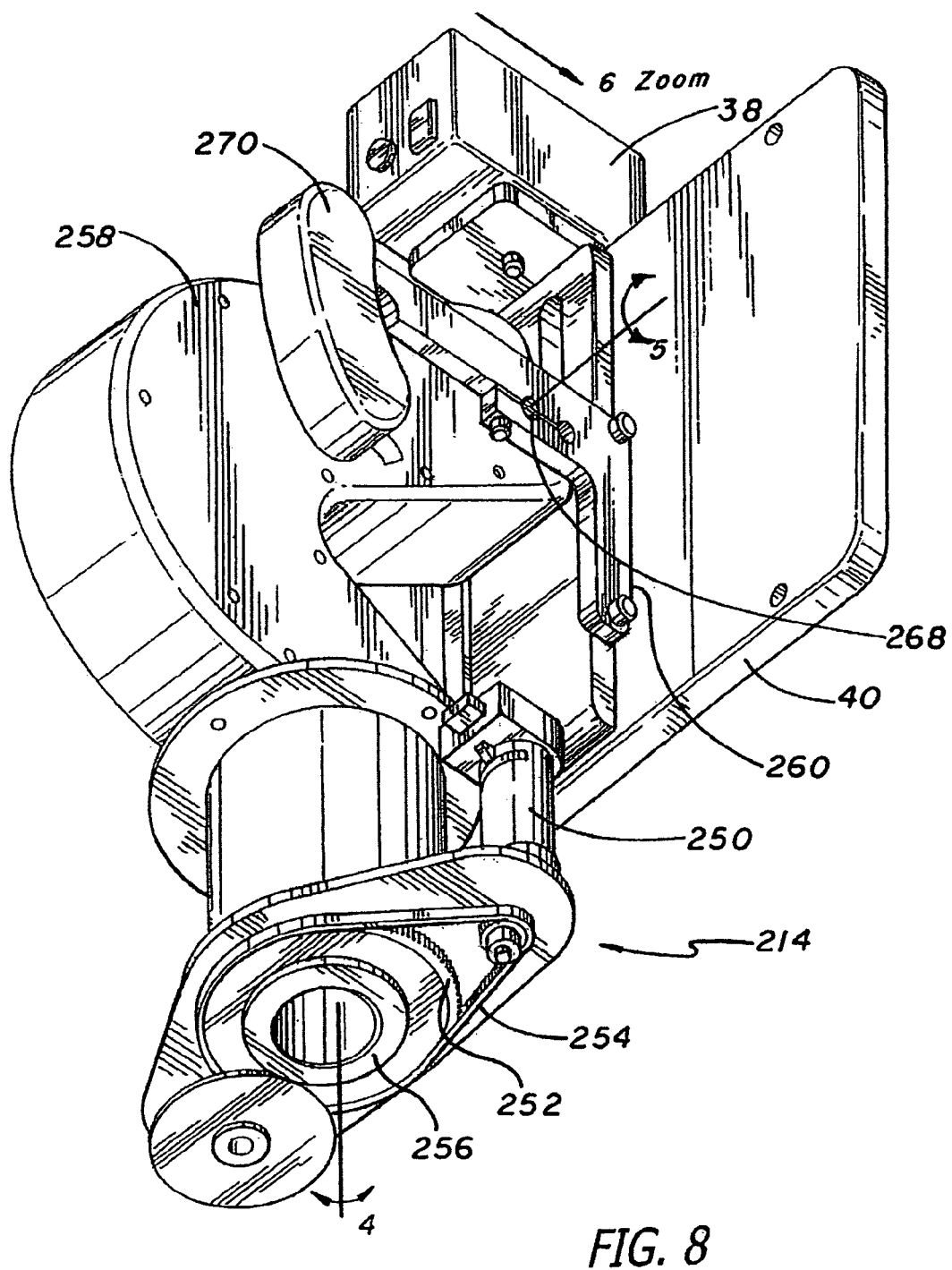
FIG. 8 is a bottom perspective view showing a pedestal assembly of the robot.

As shown in FIG. 8, the pedestal assembly 214 may include a motor 250 that is coupled to a gear 252 by a belt 254. The gear 252 is attached to a shaft 256. The shaft 256 is attached to an arm 258 that is coupled to the camera 38 and monitor 40 by a bracket 260. Activation of the motor 250 rotates the gear 252 and sleeve 256, and causes the camera 38 and monitor 40 to swivel (see also FIG. 5) as indicated by the arrows 4.

Figure 9:
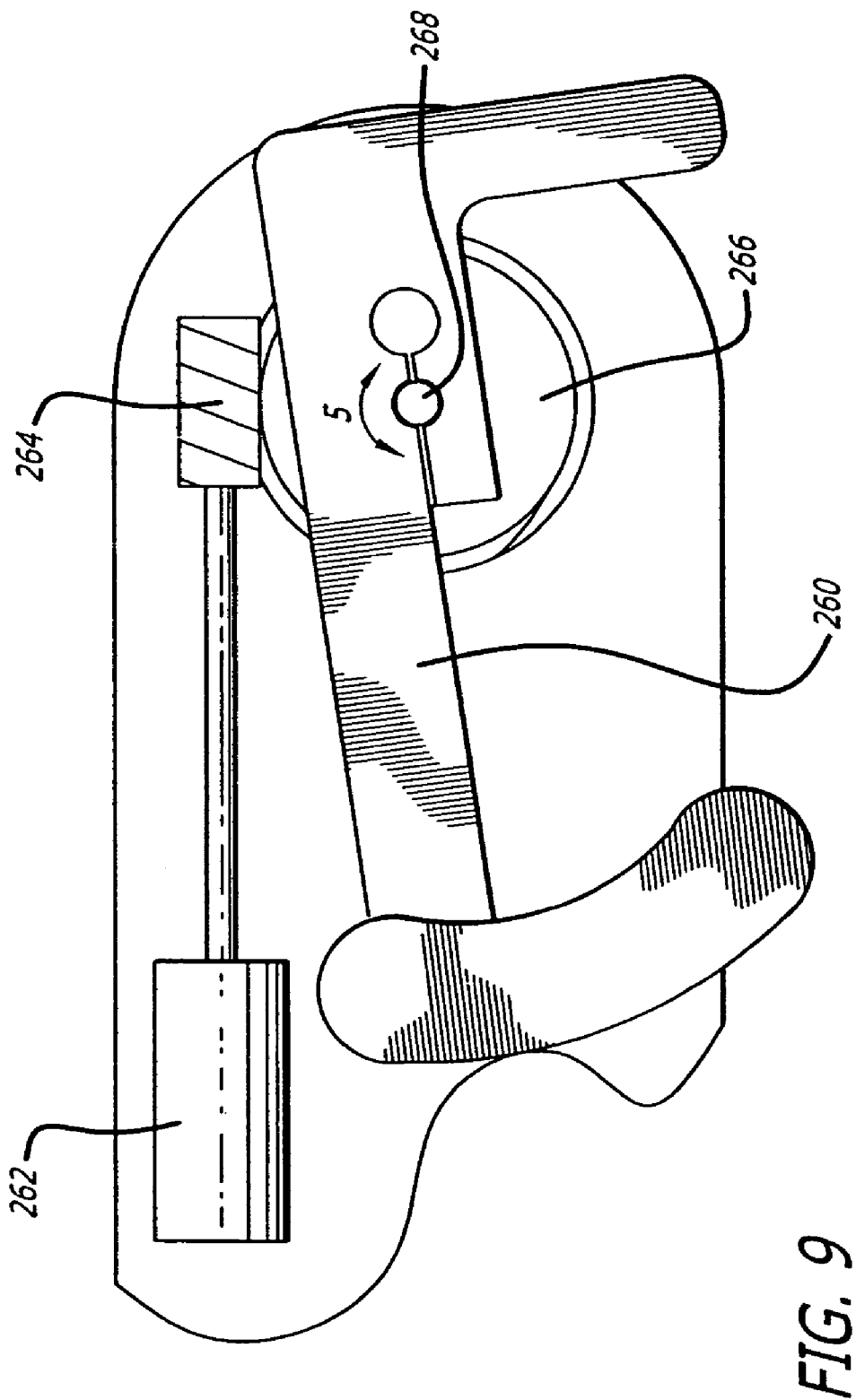
FIG. 9 is a sectional view showing an actuator of the pedestal assembly.

As shown in FIG. 9, the assembly 214 may further include a tilt motor 262 within the arm 258 that can cause the monitor 40 and camera 38 to pivot as indicated by the arrows 5. The tilt motor 262 may rotate a worm 264 that rotates a worm gear 266. The pin 268 is rigidly attached to both the worm gear 266 and the bracket 260 so that rotation of the gear 266 pivots the camera 38 and the monitor 40. The camera 38 may also include a zoom feature to provide yet another degree of freedom for the operator.

The robot 10 may be controlled by a number of different doctors. To accommodate for this the robot may have an arbitration system. The arbitration system may be integrated into the operating system of the robot 12. For example, the arbitration technique may be embedded into the operating system of the high-level controller 150.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

Message packets may be transmitted between a robot 12 and a remote station 16. The packets provide commands and feedback. Each packet may have multiple fields. By way of example, a packet may include an ID field a forward speed field, an angular speed field, a stop field, a bumper field, a sensor range field, a configuration field, a text field and a debug field.

The identification of remote users can be set in an ID field of the information that is transmitted from the remote control station 16 to the robot 12. For example, a user may enter a user ID into a setup table in the application software run by the remote control station 16. The user ID is then sent with each message transmitted to the robot.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables 1 and 2, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |

TABLE I-continued

| User | Access Control | Medical Record | Command Override | Software/Debug Access | Set Priority |
|---|---|---|---|---|---|
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user<br>Notify requesting user that system is in use<br>Set timeout | Warn current user of pending user<br>Notify requesting user that system is in use<br>Set timeout = 5 m | Warn current user of pending user<br>Notify requesting user that system is in use<br>Set timeout = 5 m<br>Call back | Warn current user of pending user<br>Notify requesting user that system is in use<br>No timeout<br>Call back |
| | Caregiver | Warn current user of pending user.<br>Notify requesting user that system is in use.<br>Release control | Not Allowed | Warn current user of pending user<br>Notify requesting user that system is in use<br>Set timeout = 5 m<br>Queue or callback | Warn current user of pending user<br>Notify requesting user that system is in use<br>Set timeout = 5 m | Warn current user of pending user<br>Notify requesting user that system is in use<br>No timeout<br>Callback |
| | Doctor | Warn current user of pending user<br>Notify requesting user that system is in use<br>Release control | Warn current user of pending user<br>Notify requesting user that system is in use<br>Set timeout = 5 m | Warn current user of pending user<br>Notify requesting user that system is in use<br>No timeout<br>Callback | Notify requesting user that system is in use<br>No timeout<br>Queue or callback | Warn current user of pending user<br>Notify requesting user that system is in use<br>No timeout<br>Callback |
| | Family | Warn current user of pending user<br>Notify requesting user that system is in use<br>Release Control | Notify requesting user that system is in use<br>No timeout<br>Put in queue or callback | Warn current user of pending user<br>Notify requesting user that system is in use<br>Set timeout = 1 m | Warn current user of pending user<br>Notify requesting user that system is in use<br>Set timeout = 5 m<br>Queue or callback | Warn current user of pending user<br>Notify requesting user that system is in use<br>No timeout<br>Callback |
| | Service | Warn current user of pending user<br>Notify requesting user that system is in use<br>No timeout | Notify requesting user that system is in use<br>No timeout<br>Callback | Warn current user of request<br>Notify requesting user that system is in use<br>No timeout<br>Callback | Warn current user of pending user<br>Notify requesting user that system is in use<br>No timeout<br>Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

Figure 10:
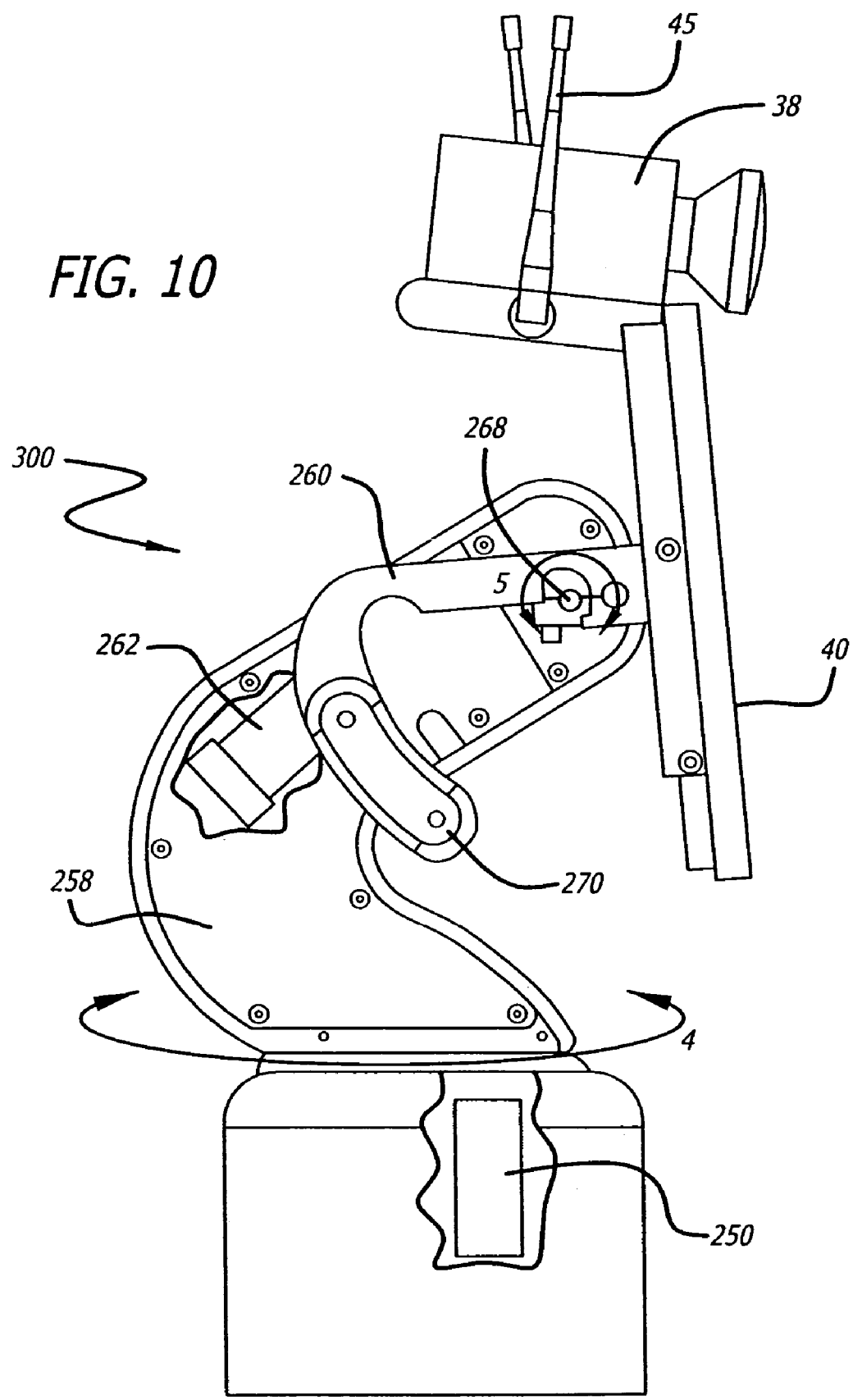
FIG. 10 is a side view of a robot head.

FIG. 10 shows a robot head 300 that can both pivot and spin the camera 38 and the monitor 40. The robot head 300 can be similar to the robot 12 but without the platform 210. The robot head 300 may have the same mechanisms and parts to both pivot the camera 38 and monitor 40 about the pivot axis 4, and spin the camera 38 and monitor 40 about the spin axis 5. The pivot axis may intersect the spin axis. Having a robot head 300 that both pivots and spins provides a wide viewing area. The robot head 300 may be in the system either with or instead of the mobile robot 12. The head 300 may be placed in a patient room to conduct two-way videoconferencing between a patient and a doctor at a remote location. The pivoting and spinning degrees of freedom allow the doctor to move the camera to follow an ambulatory patient.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for viewing a patient, comprising:
   generating a first robot movement input command at a remote station;
   transmitting the first robot movement input command;
   receiving the first robot movement input command at a robot that has a camera and a microphone;
   moving the camera to view a patient; and,
   transmitting an image of the patient and a sound of the patient from the robot to the remote station.

2. The method of claim 1, further comprising generating a second robot movement command, transmitting the second robot command and moving the robot across a floor of a medical facility.

3. The method of claim 1, wherein the robot movement input command is generated by a doctor.

4. The method of claim 1, further comprising transmitting a video image and a sound of a doctor at the remote station to the robot, the video image being displayed by a monitor of the robot, the sound being generated by a speaker of the robot.

5. The method of claim 1, wherein the robot movement input command causes the robot camera to zoom relative to the patient.

6. The method of claim 1, further comprising transmitting a video image of a medical chart from the robot to the remote station.

7. The method of claim 1, further comprising generating and transmitting a question from the remote station to the robot.

8. The method of claim 7, wherein the question is generated by a speaker of the robot.

9. The method of claim 7, wherein the question is displayed by a monitor of the robot.

10. The method of claim 1, wherein the robot movement input command is transmitted through a broadband network.

* * * * *